United States Patent
Yamamoto et al.

(10) Patent No.: US 6,512,128 B2
(45) Date of Patent: Jan. 28, 2003

(54) PROCESS USING A TITANIUM-CONTAINING SILICON OXIDE CATALYST

(75) Inventors: Jun Yamamoto, Sodegaura; Junpei Tsuji, Ichihara, both of (JP)

(73) Assignee: Sumitomo Chemical Company Limited, Osaka (JP)

( * ) Notice: Subject to any disclaimer, the term of this patent is extended or adjusted under 35 U.S.C. 154(b) by 0 days.

(21) Appl. No.: 09/967,982

(22) Filed: Oct. 2, 2001

(65) Prior Publication Data
US 2002/0037807 A1 Mar. 28, 2002

Related U.S. Application Data

(62) Division of application No. 09/364,268, filed on Jul. 3, 1999, now Pat. No. 6,323,142.

(30) Foreign Application Priority Data

| Aug. 4, 1998 | (JP) | 10-220665 |
| Jun. 3, 1999 | (JP) | 11-156393 |
| Jun. 3, 1999 | (JP) | 11-156395 |

(51) Int. Cl.$^7$ .......................................... C07D 301/19
(52) U.S. Cl. ............................................. 549/529
(58) Field of Search ........................................ 549/529

(56) References Cited

U.S. PATENT DOCUMENTS

| 3,829,392 A | 8/1974 | Wulff |
| 3,923,843 A | 12/1975 | Wulff |
| 4,367,342 A | 1/1983 | Wulff et al. |
| 5,143,879 A | 9/1992 | Whitehurt .................. 502/85 |
| 5,688,484 A | 11/1997 | Saxton et al. ............... 423/700 |
| 5,723,637 A | 3/1998 | Tsuji et al. |
| 5,783,167 A | 7/1998 | Corma Canos et al. ..... 423/701 |
| 5,795,555 A | 8/1998 | Alive et al. ................. 523/326 |
| 5,795,559 A | 8/1998 | Pinnavaia et al. .......... 423/702 |
| 6,054,112 A | 4/2000 | Hasenzahl et al. |
| 6,096,910 A | 8/2000 | Yamamoto et al. |
| 6,211,388 B1 | 4/2001 | Tsuji et al. |

FOREIGN PATENT DOCUMENTS

| EP | 0 659 685 A1 | 6/1995 |
| EP | 0 734 764 A2 | 10/1996 |
| EP | 0 838 431 A1 | 4/1998 |
| ES | 2 092 428 | 11/1996 |
| ES | 2 156 506 | 6/2001 |
| FR | 2109867 | 5/1972 |
| JP | 7-300312 | 11/1995 |

OTHER PUBLICATIONS

D.D. Eley, "Advances in Catalysis," *Microporous Crystalline Titanium Silicates*, vol. 41 (1996) edition by B. Notari, pp. 253–334.

Chen et al., "Propylene epoxidation with hydrogen peroxide catalyzed by molecular sieves containing framework titanium," *Journal of Molecular Catalysis A: Chemical 132*, (1998), pp. 281–292.

Chen et al., "Ti–containing MCM–41 catalysts for liquid phase oxidation of cyclohexene with aqueous $H_2O_2$ and tert–butyl hydroperoxide," *Catalysis Letters 50*, (1998), pp. 107–114 (D2).

Keshavaraja et al., "Synthesis, Characterization, and Catalytic Properties of Micro–Mesoporous, Amorphous Titanosilicate Catalysts," *Journal of Catalysis 157*, (1995), pp. 501–511.

Corma et al., "One step synthesis of highly active epoxidation catalysts formed by organic–inorganic Ti containing mesoporous composites,"*Chem. Commun.*, (1998), pp. 1899–1900.

*Primary Examiner*—T. A. Solola
*Assistant Examiner*—Robert W. Ramsuer
(74) *Attorney, Agent, or Firm*—Sughrue Mion, PLLC

(57) ABSTRACT

A titanium-containing silicon oxide catalyst satisfying all of the following conditions (1) to (4):

(1): an average pore size of 10 Å or more, (2): a pore size of 90% or more of the total pore volume of 5 to 200 Å, (3): a specific pore volume of 0.2 cm$^3$/g or more, and (4): a quarternary ammonium ion represented by the following general formula (I) is used as a template and then said template is removed by solvent extraction operation;

$$[NR^1R^2R^3R^4]^+ \qquad (I)$$

wherein, $R^1$ represents a linear or branched hydrocarbon chain having 2 to 36 carbon atoms, and $R^2$ to $R^4$ represent an alkyl group having 1 to 6 carbon atoms, a method for producing said catalyst, and a method for producing propylene oxide by reacting propylene with a hydroperoxide, except for ethylbenzene hydroperoxide, in the presence of said catalyst.

10 Claims, No Drawings

PROCESS USING A TITANIUM-CONTAINING SILICON OXIDE CATALYST

This is a divisional of application Ser. No. 09/364,268 filed Jul. 30, 1999, now U.S. Pat. No. 6,323,147.

BACKGROUND OF THE INVENTION

1. Field of the Invention

The present invention relates to a titanium-containing silicon oxide catalyst, a method for producing the same, and a method for producing propylene oxide. More particularly, the present invention relates to a titanium-containing silicon oxide catalyst which can produce propylene oxide by reacting propylene with a hydroperoxide, except for ethylbenzene hydroperoxide, in high yield and high selectivity, a method for producing said catalyst, and a method for producing propylene oxide.

2. Description of the Related Art

It is known that a titanium-containing silicon oxide can be produced by using a quarternary ammonium ion as a template. As a titanium-containing silicon oxide having an average pore size of 10 Å or more, Ti-MCM41 disclosed in U.S. Pat. No. 5,783,167, Ti-MCM48 disclosed in JP 07300312 A and the like are known. These known titanium-containing silicon oxides having large pores of 10 Å or more are obtained by removing the template by calcining. When these titanium-containing silicon oxides are used as a catalyst in an epoxidation reaction, catalytic activity is not in the satisfactory level. A catalyst having higher activity has been desired.

SUMMARY OF THE INVENTION

Under these circumstances, the present inventors have intensively studied for a catalyst having a high catalytic activity in an epoxidation reaction, and have found that a catalyst obtained by removing a template via extracting in a solvent has a high catalytic activity in an epoxidation reaction. The present inventors thus completed the present invention.

An object of the present invention is to provide a titanium-containing silicon oxide catalyst which can produce propylene oxide by reacting propylene with a hydroperoxide, except for ethylbenzene hydroperoxide, a method for producing said catalyst, and a method for producing propylene oxide in high yield and high selectivity.

Namely, the present invention relates to a titanium-containing silicon oxide catalyst satisfying all of the following conditions (1) to (4):

(1): An average pore size of 10 Å or more.

(2): A pore size of 90% or more of the total pore volume of 5 to 200 Å.

(3): A specific pore volume of 0.2 cm³/g or more.

(4): A quarternary ammonium ion represented by the following general formula (I) is used as a template and then said template is removed by solvent extraction operation;

$$[NR^1R^2R^3R^4]^+ \quad (I)$$

(wherein, $R^1$ represents a linear or branched hydrocarbon chain having 2 to 36 carbon atoms, and $R^2$ to $R^4$ represent an alkyl group having 1 to 6 carbon atoms).

The present invention also relates to a method for producing said catalyst, wherein said method comprises the following steps of;

mixing and stirring a silica source, titanium source and a quarternary ammonium ion as a template in a solvent to obtain a solid containing a catalyst component and the template, and extracting the obtained solid in a solvent to obtain a catalyst by removing the template.

The present invention further relates to a method for producing propylene oxide by reacting propylene with a hydroperoxide, except for ethylbenzene hydroperoxide.

DETAILED DESCRIPTION OF THE PREFERRED EMBODIMENTS

The catalyst used in the present invention is a catalyst comprising a titanium-containing silicon oxide satisfying all of the following conditions (1) to (4). The object of the present invention can be fully accomplished by using said catalyst. The main object of the present invention is to produce propylene oxide by reacting propylene with a hydroperoxide, except for ethylbenzene hydroperoxide, in high yield and high selectivity.

The condition (1) is that an average pore size of the catalyst is 10 Å or more.

The condition (2) is that a pore size of 90% or more of the total pore volume of the catalyst is 5 to 200 Å.

The condition (3) is that a specific pore volume of the catalyst is 0.2 cm³/g or more. The specific pore volume means pore volume per 1 g of the catalyst.

Measurements of these conditions (1) to (3) can be conducted by known methods such as a physical absorption method using gases such as nitrogen, argon and the like.

The condition (4) is that the catalyst is obtained by using a quarternary ammonium ion represented by the following general formula (I) as a template and then removing said template by a solvent extraction operation;

$$[NR^1R^2R^3R^4]^+ \quad (I)$$

(wherein, $R^1$ represents a linear or branched hydrocarbon chain having 2 to 36 carbon atoms, and $R^2$ to $R^4$ represent an alkyl group having 1 to 6 carbon atoms).

The condition (4) will be illustrated in detail herein with regard to a method for producing said catalyst.

A catalyst of the present invention preferably has at least one peak showing an interplanar spacing (d) of larger than 18 Å, or no peak showing an interplanar spacing (d) in a X-ray diffraction (XRD). The peak showing an interplanar spacing (d) as herein referred to means a peak derived from the crystallinity and regularity of a solid, and a broad peak derived from an amorphous part may exist. When, a peak showing an interplanar spacing (d) of larger than 18 Å exists in a X-ray diffraction, it is preferable that this peak is a part of a peak group showing the structure of a hexagonal system.

The catalyst of the present invention preferably has an absorption peak in the range of 960±5 cm⁻¹ in the infrared absorption spectrum. This peak is considered to correspond to titanium introduced into a silica skeleton.

The catalyst of the present invention can be produced by the following method comprising the following steps.

The first step: A step in which a silica source, titanium source and a quarternary ammonium ion as a template are mixing and stirring in a solvent to obtain a solid containing a catalyst component and the template.

The second step: A step in which a catalyst is obtained by extracting the obtained solid in a solvent to remove the template.

The first step is a step which a silica source, a titanium source and a quarternary ammonium ion as a template are mixing and stirring in a solvent to obtain a solid containing a catalyst component and the template. When a reagent to be used is solid, it may be used by dissolving in a solvent, or dispersing in a solvent.

Examples of the silica source include amorphous silica and alkoxysilane such as tetramethyl orthosilicate, tetraethyl orthosilicate, tetrapropyl orthosilicate and the like.

Examples of the titanium source include titanium alkoxides such as tetramethyl titanate, tetraethyl titanate, tetrapropyl titanate, tetraisopropyl titanate, tetrabutyl titanate, tetraisobutyl titanate, tetra-2-ethylhexyl titanate, tetraoctadecyl titanate, and titanium (IV) oxyacetylacetonate, titanium (IV) diisopropoxybisacetyl acetonate and the like, and titanium halides such as titanium tetrachloride, titanium tetrabromide, titanium tetraiodide and the like.

As a template, a quarternary ammonium ion represented by the following general formula (I) is used.

$$[NR^1R^2R^3R^4]^+ \quad (I)$$

(wherein, $R^1$ represents a linear or branched hydrocarbon chain having 2 to 36 carbon atoms, and $R^2$ to $R^4$ represent an alkyl group having 1 to 6 carbon atoms).

$R^1$ represents a linear or branched hydrocarbon chain having 2 to 36 carbon atoms, preferably 10 to 18 carbon atoms.

$R^2$ to $R^4$ represent an alkyl group having 1 to 6 carbon atoms, and preferably each of $R^2$ to $R^4$ is a methyl group.

Specific examples of the quarternary ammonium ion represented by the general formula (I) include cations such as hexadecyltrimethylammonium, dodecyltrimethylammonium, benzyltrimethylammonium, dimethyldidodecylammonium, hexadecylpyridinium, and the like.

Examples of the solvent include water and alcohol such as methanol, ethanol, n-propanol, 2-propanol, n-butanol, sec-butanol, t-butanol, vinyl alcohol, allyl alcohol, cyclohexanol, benzyl alcohol and the like, and diols, or a mixture thereof, and the like.

A suitable mixing ratio of a solvent to silica source varies according to a kind of silica source to be used. When using alkoxy silane and diluting it by using an alcohol having the same or similar property as an alkoxide ligand, a catalyst having no peak showing an interplanar spacing (d) in X-ray diffraction can be obtained.

The amount used of the titanium source based on the silica source is preferably from $10^{-5}$ to 1, more preferably from 0.00008 to 0.4 in terms of molar ratio. The amount used of the quarternary ammonium ion based on the total amount of silica source and titanium source is preferably from $10^{-2}$ to 2 in terms of molar ratio.

For promoting the reaction of the silica source and the titanium source, it is preferable to impart alkalinity or acidity to the mixed solution. As the alkali source, quarternary ammonium hydroxides are preferable, and examples thereof include tetramethylammonium hydroxide, tetraethylammonium hydroxide, tetrapropylammonium hydroxide and the like. Examples of the acid include inorganic acids such as hydrochloric acid, sulfuric acid, nitric acid and the like, and organic acids such as formic acid, acetic acid, propionic acid and the like.

The mixing and stirring temperature is usually from −30 to 100° C. Solid is formed by mixing and stirring, and the solid may be aged for further growth thereof. The aging time is usually 180 hours or less, and the aging temperature is usually from 0 to 200° C. When heating is required in aging, it is preferable that the mixture is transferred into a pressure vessel and heating is conducted in a closed pressure vessel for avoiding vaporization of the solvent.

The second step is a step in which a catalyst is obtained by extracting the obtained solid in a solvent to remove the template.

A technique extracting a template in a solvent is reported by Whitehurst et al. (see U.S. Pat. No. 5,143,879)

A solvent used in extraction may include a solvent which can dissolve a compound used as the template. Oxa and/or oxo substituted hydrocarbons having carbon atoms of 1 to about 12 in the liquid state at room temperature are usually used as a solvent. Suitable examples of such solvents include alcohols, ketones, (acyclic and cyclic) ethers, esters.

Examples thereof include a hydrocarbon substituted by hydroxyl group such as methanol, ethanol, ethylene glycol, propylene glycol, isopropanol, n-butanol or octanol, a hydrocarbon substituted by oxo group such as acetone, diethyl ketone, methyl ethyl ketone or methyl isobutyl ketone, an ether of a hydrocarbon such as diisobutyl ether or tetrahydrofuran, an ester of a hydrocarbon such as methyl acetate, ethyl acetate, butyl acetate or butyl propionate, and the like.

The weight ratio of the solvent to the catalyst is usually from 1 to 1000, preferably from 10 to 300.

For improving efficiency of the extraction, acids or salts thereof may be added to these solvents.

Examples of acids used include inorganic acids such as hydrochloric acid, sulfuric acid, nitric acid, bromic acid and the like, organic acids such as formic acid, acetic acid, propionic acid and the like. Examples of salts thereof include alkali metal salt, alkaline earth metal salt, ammonium salt and the like.

The concentration of acids or salts thereof to be added is preferably 10 mol/l or less, further preferably 1 mol/l or less. When the concentration of acids or salts thereof to be added is too high, catalytic activity may be lowered by eluting titanium in the catalyst.

A catalyst having no peak showing an interplanar spacing (d) in X-ray diffraction can be obtained, when the weight ratio of water in a solvent to a catalyst is 0.8 or more. The weight ratio is varied depending on a extraction temperature or acid content.

After fully mixing a catalyst with a solvent, a liquid portion is separated by filtration, decantation and the like. This operation is repeated required times. The catalyst can be obtained by extracting the catalyst layer with a solvent for washing. The termination of washing can be known by analyzing the liquid portion. The extraction temperature is preferably 0 to 200° C., further preferably 20 to 100° C.

Instead of using the above-mentioned solvent, extraction can be conducted by using a super critical fluid. As a super critical fluid, carbon dioxide is preferable. The critical temperature of carbon dioxide is about 31° C. or more. Therefore, the extraction temperature is preferably 31 to 100° C., further preferably 35 to 60° C. The critical pressure of carbon dioxide is about 7.4 MPa, so the extraction pressure is preferably 10 to 30 MPa. The amount of super critical carbon dioxide used for extraction is preferably 50 to 500 g/min. per 1 liter of catalyst. The extraction time is preferably 4 to 20 hours.

The resulted solid after extraction may be dried. Drying is conducted preferably at a temperature of 10to 800° C., further preferably 50 to 300° C. under an atmosphere of non-reducing gas such as nitrogen, argon, carbon dioxide, or oxygen-containing gas such as air.

In order to obtain a catalyst of the present invention, it is preferable that the following third step is conducted following the above-mentioned first and second steps.

The third step: A step in which a silylation treated catalyst is obtained by a silylation treatment of the catalyst obtained in the second step. The silylation treatment is usually conducted by contacting the catalyst obtained in the second step with a silylation agent, and converting a hydroxyl group existing on the surface of the catalyst into a silyl group.

Examples of the silylation agent include an organic silane, organic silylamine, organic silylamide and derivatives thereof, and organic silazane and other silylation agents.

Examples of the organic silane include chrolotrimethylsilane, dichlorodimethylsilane, chlorobromodimethylsilane, nitrotrimethylsilane, chlorotriethylsilane, iododimethylbutylsilane, chlorodimethylphenylsilane, dichlorodimethylsilane, dimethyl-n-propylchlorosilane, dimethylisopropylchlorosilane, t-butyldimethylchlorosilane, tripropylchlorosilane, dimethyloctylchlorosilane, tributylchlorosilane, trihexylchlorosilane, dimetylethylchlorosilane, dimethyloctadecylchlorosilane, n-butyldimethylchlorosilane, bromomethyldimethylchlorosilane, chloromethyldimethylchlorosilane, 3-chloropropyldimethylchlorosilane, dimethoxymethylchlorosilane, dimethylphenylchlorosilane, triethoxychlorosilane, dimethylphenylchlorosilane, methylphenylvinylchlorosilane, benzyldimethylchlorosilane, diphenyldichlorosilane, diphenylmethylchlorosilane, diphenylvinylchlorosilane, tribenzylchlorosilane, 3-cyanopropyldimethylchlorosilane.

Examples of the organic silylamine include N-trimethylsilylimidazole, N-t-butyldimethylsilylimidazole, N-dimethylethylsilylimidazole, N-dimethyl-n-propylsilylimidazole, N-dimethylisopropylsilylimidazole, N-trimethylsilyldimethylamine, N-trimethylsilyldiethylamine, N-trimethylsilylpyrrole, N-trimethylsilylpyrrolidine, N-trimethylsilylpiperidine, 1-cyanoethyl(diethylamino)dimethylsilane, pentafluorophenyldimethylsilylamine.

Examples of the organic silylamide and derivatives include N,O-bistrimethylsilylacetamide, N,O-bistrimethylsilyltrifluoroacetamide, N-trimethylsilylacetamide, N-methyl-N-trimethylsilylacetamide, N-metyl-N-trimethylsilyltrifluoroacetamide, N-methyl-N-trimethylsilylheptafluorobutylamide, N-(t-butyldimethylsilyl)-N-trifluoroacetamide, N,O-bis(diethylhydrosilyl)trifluoroacetamide.

Examples of the organic silazane include hexamethyldisilazane, heptamethyldisilazane, 1,1,3,3-tetramethyldisilazane, 1,3-bis(chloromethyl)tetramethyldisilazane, 1,3-divinyl-1,1,3,3-teteramethyldisilazane, 1,3-diphenyltetramethyldisilazane.

Examples of the other silylation agent include N-methoxy-N,O-bistrimethylsilyltrifluoroacetamide, N-methoxy-N,O-bistrimethylsilyl carbamate, N,O-bistrimethylsilyl sulfamate, trimethylsilyltrifluoromethane sulfonate, N,N'-bistrimethylsilylurea. The preferable silylation agent is hexamethyldisilazane.

As a catalyst thus obtained has a large surface area and a highly dispersed titanium active point, the catalyst can be used for a selective oxidation reaction, for example, an epoxidation reaction of an olefin, and various kinds of oxidation reactions. An acidic point of the catalyst can strengthen by adding the third component such as alumina and the like according to necessity. The strengthened catalyst can be used for an alkylation reaction and a catalytic modified reaction and the like.

A catalyst of the present invention is suitably used for the production of propylene oxide by reacting propylene with a hydroperoxide, except for ethylbenzene hydroperoxide.

Examples of a hydroperoxide, except for ethylbenzene hydroperoxide, include organic hydroperoxides and hydrogen peroxide.

Organic hydroperoxides are represented by the following general formula;

(R represents a hydrocarbon group having one valence).

An organic hydroperoxide is reacted with olefin type compound to produce an oxirane compound and a compound, R—OH. Group "R" is preferably a group having carbon atoms of 3 to 20, more preferably a hydrocarbon group having carbon atoms of 3 to 10, a secondary alkyl group, tertiary alkyl group, secondary aralkyl group, or tertiary aralkyl group. Among them, a tertiary alkyl group, secondary aralkyl group, and tertiary aralkyl group are most preferable, and concrete examples thereof include a tertiary butyl group, tertiary pentyl group, cyclopentyl group, 2-phenylpropyl-2 group, and various tetralinyl groups produced by abstracting hydrogen atoms from a tetralin molecule.

When using cumene hydroperoxide as an organic hydroperoxide, the resulting hydroxyl compound is 2-phenyl-2-propanol. This can be converted to α-methyl styrene by dehydration reaction. α-methyl styrene is a industrially useful substance.

When using tertiary pentylhydroperoxide as an organic hydroperoxide, the resulting tertiary amylene by dehydration reaction of tertiary pentyl alcohol is a useful substance as a precursor of isoprene. Tertiary pentyl alcohol is a useful substance as a precursor of methyl tertiary pentyl ether which is an octane booster.

Tertiary butyl alcohol obtained by using tertiary butyl hydroperoxide as an organic hydroperoxide is a useful substance as a precursor of methyl tertiary butyl ether which is an octane booster.

Hydrogen peroxide is a compound represented by the chemical formula HOOH, and can be obtained usually in the form of an aqueous solution. It reacts with an olefin type compound to form an oxirane compound and water.

The organic hydroperoxide and hydrogen peroxide, which are used as a raw material, may be a thin or dense purified or non-purified substance.

The epoxidation reaction can be conducted by contacting propylene and an organic hydroperoxide, except for ethylbenzene hydroperoxide, with a catalyst. The epoxidation reaction may also be carried out in a liquid phase by using a solvent and/or a diluent. This solvent and diluent are preferably a substance which are liquid under the pressure and temperature when the reaction is conducted, and substantially inactive against the reactants and product. The solvent may be a substance existing in the hydroperoxide solution. For example, when cumene hydroperoxide comprises a mixture of cumene hydroperoxide and cumene, which is a raw material thereof, said cumene hydroperoxide can be used as a substitute for the solvent without specifically adding a solvent.

The reaction temperature of epoxidation is usually from 0 to 200° C., preferably from 25 to 200° C. The reaction pressure is preferably from 100 to 10000 kPa.

A liquid mixture containing desired product is easily separated from a catalyst composition after the termination of epoxidation reaction. Then the liquid mixture is purified by a suitable method to obtain desired propylene oxide. Purification includes fractional distillation, fractional extraction, filtration, washing and the like. The solvent, the catalyst, non-reacted propylene and non-reacted hyperoxide can be used again by recycling. The method of the present invention can be advantageously carried out by using a catalyst in the form of a slurry or a fixed bed. In the case of a large scale of industrial operation, it is preferable to use a catalyst in the form of a fixed bed. The method of the present invention can be carried out by a batchwise method, semi-continuous method or continuous method. When a solution containing a reactant is introduced through a fixed bed, a liquid mixture obtained from a reaction solution does not contain catalyst at all or contains substantially no catalyst.

Propylene oxide can be converted to an industrially useful product by a polymerization reaction or copolymerization reaction.

As described above, there are provided herein a titanium-containing silicon oxide catalyst that can produce propylene oxide by reacting propylene with a hydroperoxide, except for ethylbenzene hydroperoxide, in high yield and high selectivity, a method for producing said catalyst, and a method for producing propylene oxide.

EXAMPLE

The present invention will be described by way of examples, which should not be construed as limiting the scope of the invention.

Example 1
Preparation of a Catalyst

With 175 g of water was mixed 28 g of cetyltrimethylammonium bromide and 48 g of 25 wt % aqueous tetramethylammonium hydroxide solution, and to this mixture was added a mixture of 77 g of tetramethyl orthosilicate and 6.3 g of 75 wt % titanium (IV) diisopropoxy bisacetylacetonate at room temperature. The mixture was allowed to continue to stir for 3 hours, then, the resulting precipitate was filtered off and washed with water. The washing was conducted until the washing solution became neutral. The filtered precipitate was put into a flask and stirred to mix with 500 ml of a mixed solution of hydrochloric acid/ethanol (hydrochloric acid (0.1 mol/l)). The solution was heating at 60° C. for one hour with stirring, and cooling to 40° C. or less for 5 hour, then filtered to remove solvent. The same procedure was repeated once more. Finally, the filtered white solid was transferred to a tubular furnace, heated at 150° C. for 5 hours under nitrogen flow. This substance (5 g), hexamethyldisilazane (3.4 g) and toluene (50 g) were mixed, and the mixture was heated for 1 hour under reflux with stirring. Liquid was removed by filtration from the mixture. It was washed with toluene (100 g), and dried under reduced pressure (120° C., 10 mmHg, 3 hours) to obtain a catalyst. Thus obtained catalyst had a specific surface area of 936 m²/g, an average pore size of 30 Å and a pore volume of 0.7 cc/g, and a pore size distribution range of from 5 Å to 80 Å.

Synthesis of Propylene Oxide (PO)

Thus obtained catalyst was evaluated by a batch reaction of 41% cumene hydroperoxide (CHPO) with propylene. The obtained catalyst (0.75 g), propylene (13 g) and cumene hydroperoxide (17 g) were charged in an autoclave made of stainless steel, and they were reacted at 80° C. for 90 minutes. The reaction results are shown in Table 1.

Comparative Example 1
Preparation of Titanium Supported Catalyst

Acetylacetone (3.2 g) was slowly added dropwise to a solution of tetraisopropyl titanate (4.4 g) in isopropanol (20 ml) with stirring under nitrogen flow, then, the mixture was stirred at room temperature for 30 minutes. To a mixture of a commercially available silica gel (10 to 20 mesh, surface area 326 m²/g, average pore diameter 100 Å)(50 g) and isopropanol (230 ml) were added the above-described solution dropwise, then, the mixture was stirred at room temperature for 1 hour, and filtered. The solid portion was washed with isopropanol three times (total 250 ml). The solid portion was dried at 150° C. for 2 hours under air atmosphere. The solid portion was further calcined at 600° C. for 4 hours under air atmosphere. This substance (10 g), hexamethyldisilazane (4 g) and toluene (50 g) were mixed and stirred, and heated for 1 hour under reflux. Liquid was removed from the mixture by filtration. It was washed with toluene (100 g) and dried under reduced pressure (120° C., 10 mmHg, 3 hours) to obtain a catalyst. Thus obtained catalyst had a specific surface area of 244 m²/g, an average pore size of 148 Å and a pore volume of 0.9 cc/g, and a pore size distribution range of from 5 Å to 80 Å.

The reaction was evaluated in the same manner as in Example 1. The results of the Epoxidation reaction are shown in Table 1.

TABLE 1

|  | Example 1 | Comparative example 1 |
|---|---|---|
| Catalyst properties |  |  |
| Average pore size Å | 30 | 148 |
| Pore distribution range Å | 5*¹ –80 | 5*¹ –200 |
| Specific pore volume cm³/g | 0.7 | 0.9 |
| Use of template | Yes | No |
| X-ray diffraction |  |  |
| Peak showing interplanar spacing d > 18 Å | Yes | No |
| Reaction results |  |  |
| CHPO conversion % | 81.3 | 54.7 |
| PO selectivity % | 88.9 | 85.8 |

*¹The minimum value of pore size distribution is the limit of measurement according to the nitrogen absorption method utilized.

What is claimed is:

1. A method for producing propylene oxide by reacting propylene with a hydroperoxide, except for ethylbenzene hydroperoxide, in the presence of a titanium-containing silicon oxide catalyst satisfying all of the following conditions (1) to (4):

(1): an average pore size of 10 Å or more,
(2): a pore size of 90% or more of the total pore volume of 5 to 200 Å,
(3): a specific pore volume of 0.2 cm³/g or more, and
(4): a quaternary ammonium ion represented by the following general formula (I) is used as a template and the said template is removed by solvent extraction operation;

$$[NR^1R^2R^3R^4]^+ \tag{I}$$

wherein, $R^1$ represents a linear or branched hydrocarbon chain having 10 to 36 carbon atoms, and $R^2$ to $R^4$ represent an alkyl group having 1 to 6 carbon atoms, and wherein the catalyst has no peak showing an interplanar spacing (d) in a X-ray diffraction.

2. A method for producing propylene oxide by reacting propylene with a hydroperoxide, except for ethylbenzene hydroperoxide, in the presence of a titanium-containing silicon oxide catalyst satisfying all of the following conditions (1) to (4):

(1): an average pore size of 10 Å or more, (2): a pore size of 90% or more of the total pore volume of 5 to 200 Å, (3): a specific pore volume of 0.2 cm$^3$/g or more, and (4): a quaternary ammonium ion represented by the following general formula (I) is used as a template and the said template is removed by solvent extraction operation;

$$[NR^1R^2R^3R^4]^+ \qquad (I)$$

wherein, R$^1$ represents a linear or branched hydrocarbon chain having 10 to 36 carbon atoms, and R$^2$ to R$^4$ represent an alkyl group having 1 to 6 carbon atoms, and wherein the catalyst has at least one peak showing an interplanar spacing (d) of larger than 18 Å in a X-ray diffraction, the peak is a part of the peak group showing hexagonal system.

3. The method according to claim 1, wherein the catalyst has an absorption peak in the range of 960±5 cm$^{-1}$ in the infrared ray absorption spectrum.

4. The method according to claim 2, wherein the catalyst has an absorption peak in the range of 960±5 cm$^{-1}$ in the infrared ray absorption spectrum.

5. The method according to claim 1, wherein the hydroperoxide is an organic hydroperoxide.

6. The method according to claim 2, wherein the hydroperoxide is an organic hydroperoxide.

7. The method according to claim 1, wherein the hydroperoxide is cumene hydroperoxide.

8. The method according to claim 2, wherein the hydroperoxide is cumene hydroperoxide.

9. The method according to claim 1, wherein the hydroperoxide is hydrogen peroxide.

10. The method according to claim 2, wherein the hydroperoxide is hydrogen peroxide.

* * * * *

UNITED STATES PATENT AND TRADEMARK OFFICE
CERTIFICATE OF CORRECTION

PATENT NO.   : 6,512,128 B2
DATED        : January 28, 2003
INVENTOR(S)  : Jun Yamamoto and Junpei Tsuji It is certified that error appears in the above-identified patent and that said Letters Patent is hereby corrected as shown below:

<u>Title page,</u>
Item [62], Related U.S. Application Data, delete "filed on Jul. 3, 1999, now Pat. No. 6,323,142" and insert -- filed on Jul. 30, 1999, now Pat. No. 6,323,147 --.

Signed and Sealed this

Seventeenth Day of June, 2003

JAMES E. ROGAN
*Director of the United States Patent and Trademark Office*